US005665713A

United States Patent [19]
Camden

[11] Patent Number: 5,665,713
[45] Date of Patent: Sep. 9, 1997

[54] PHARMACEUTICAL COMPOSITION FOR INHIBITING THE GROWTH OF VIRUSES AND CANCERS

[75] Inventor: James Berger Camden, West Chester, Ohio

[73] Assignee: Procter & Gamble Company, Cincinnati, Ohio

[21] Appl. No.: 420,940

[22] Filed: Apr. 12, 1995

[51] Int. Cl.$^6$ ................................................. A61K 31/66
[52] U.S. Cl. .............................................. 514/76; 514/114
[58] Field of Search .................. 514/76, 114; 558/169; 562/17

[56] References Cited

U.S. PATENT DOCUMENTS

| | | | |
|---|---|---|---|
| 3,799,758 | 3/1974 | Franz | 71/86 |
| 3,853,530 | 12/1974 | Franz | 71/76 |
| 3,903,297 | 9/1975 | Robert | 424/305 |
| 4,408,052 | 10/1983 | Hozumi | 546/22 |
| 4,542,219 | 9/1985 | Hozumi | 546/22 |
| 4,544,512 | 10/1985 | Hozumi | 260/925 |
| 4,634,693 | 1/1987 | Cardarelli | 514/169 |
| 4,649,203 | 3/1987 | Nojma et al. | 548/122 |
| 4,775,758 | 10/1988 | Nojma et al. | 546/22 |
| 4,866,059 | 9/1989 | Temple | 514/248 |
| 4,994,591 | 2/1991 | Anderson | 556/137 |
| 5,114,951 | 5/1992 | King | 43/42 |

FOREIGN PATENT DOCUMENTS 07453  8/1989  WIPO.

OTHER PUBLICATIONS

Dus et al., "Cytostatic Activity in vitro of Phosphonic Acid Derivatives" Arch. Immuno. Ther. Exp. vol. 33, No. 219, pp. 325–329 (1985).

Bandurina, "Synthesis and Antitumor Activity of Aminophosphonic Acids", Pharm. Chem. J. vol. 12, pp. 1428–1431 (1978).

Mochida et al, "Chemical Control of Green Leafhoppers to Prevent Virus Diseases, especially tungro Disease, on Susceptible Intermediate Rice Cultivars in the Tropics" Trop. Agric. Res. Ser., vol. 19, pp. 195–208.

U.S. application No. 08/420,913, J. B. Camden, filed Apr. 12, 1995.

U.S. application No. 08/420,935, J. B. Camden, filed Apr. 12, 1995.

*Primary Examiner*—David Buttner
*Attorney, Agent, or Firm*—Rose Ann Dabek; Jacobus C. Rasser

[57] ABSTRACT

This invention is a pharmaceutical composition that inhibits the growth of cancers and tumors in mammals, particularly in human and warm blooded animals. The composition is also effective against viruses. The composition contains N-phosphonoglycine derivatives which are systemic herbicides.

18 Claims, No Drawings

PHARMACEUTICAL COMPOSITION FOR INHIBITING THE GROWTH OF VIRUSES AND CANCERS

TECHNICAL FIELD

This invention is a pharmaceutical composition that inhibits the growth of cancers and tumors in mammals, particularly in human and warm blooded animals. The composition is also effective against viruses. The composition contains N-phosphonoglycine derivatives which are systemic herbicides.

BACKGROUND OF THE INVENTION

Cancers are the leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents which target especially rapidly dividing cells (both tumor and normal) have been used. Alternatively, materials that were cytotoxic to tumor cells while exerting mild effects on normal cells would be desirable. Therefore, it is an object of this invention to provide a pharmaceutical composition that is effective in inhibiting the growth of tumors and cancers in mammals with mild or no effects on normal cells.

More specifically, it is an object of this invention to provide an anti-cancer composition comprising a pharmaceutical carrier and an N-phosphonoglycine derivative as defined herein along with a method of treating such cancers.

These compositions are also effective against viruses. The pharmaceutical compositions can be used to treat vital infections. Therefore, it is a further object of this invention to provide a method of treating viral infections such as HIV, influenza and rhinoviruses.

These and other objects will become evident from the following detailed description of this inventions.

SUMMARY OF THE INVENTION

A pharmaceutical composition for treatment of mammals, and in particular, warm blooded animals and humans, comprising a pharmaceutical carrier and an effective amount anti-cancer compound selected from the group consisting of N-phosphonoglycine derivatives of the formula:

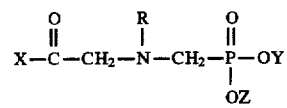

wherein X is selected from the group consisting of hydroxy, alkoxy or chloroxy up to 12 carbon atoms; lower alkenoxy, cyclohexyloxy, morpholino, pyrrlidinyl, piperidino and NHR'; Y and Z each independently selected from hydrogen and lower alkyl; and R is selected from the group consisting of hydrogen, formyl, acetyl, benzoyl, nitrobenzoyl and chlorinated benzoyl; and R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, acetate, solicylate, pyridine, atomic number of up to 30, hydrochloride, acetate, solicylate, pyridine, ammonium, lower aliphatic hydrocarbon amine, lower alkanol amine and aniline.

These compositions can be used to inhibit the growth of cancers and other tumors in humans or animals by administration of an effective amount of the N-phosphonogylcine derivatives either orally, rectally, topically or parenterally, intravenously, or by direct injection near or into the tumor. These compositions are effective in killing or slowing the growth of tumors, yet are safer than adriamycin on normal, healthy cells.

DETAILED DESCRIPTION OF THE INVENTION

A. Definitions:

As used herein, the term "comprising" means various components can be conjointly employed in the pharmaceutical composition of this invention. Accordingly, the terms "consisting essentially of" and "consisting of" are embodied in the term comprising.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutical addition salts" includes a pharmaceutically acceptable salt of the anti-cancer compound with an organic or inorganic acid and the amine salts of the acid.

As used herein, a "pharmaceutical carrier" is a pharmaceutically acceptable solvent, suspending agent or vehicle for delivering the anti-cancer agent to the animal or human. The carrier may be liquid or solid and is selected with the planned manner of administration in mind.

As used herein, "cancer" refers to all types of cancers or neoplasm or tumors found in mammals.

As used herein, the "anti-cancer compounds" are the N-phosphonoglycines, and their salts. The exact N-phosphonoglycines are described in detail below. The preferred material is the products sold under the name glyphosate® or Roundup® by Monsanto. It is N-(phosphonomethyl) glycine.

As used herein, "viruses" includes viruses which cause diseases in warm blooded animals including HIV, influenza, rhinoviruses, herpes and the like.

B. THE ANTI-CANCER COMPOUNDS

The anti-cancer compounds are N-phosphonoglycine derivatives which are known for their herbicidal activities. They are systemic herbicides used to prevent and eradicate certain plants or weeds. Systemic herbicides are differentiated from other herbicides by their ability to move through the plant. It is not a requirement of this invention that the anti-cancer compounds have this ability.

The compounds have the following structure

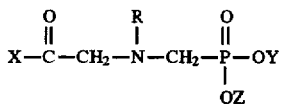

wherein X is selected from the group consisting of hydroxy, thioyl, alkoxy or chloroxy up to 12 carbon atoms; lower alkenoxy, cyclohexyloxy, morpholino, pyrrlidinyl, piperidino and NHR'; Y and Z each independently selected from hydrogen and lower alkyl; and R is selected from the group consisting of hydrogen, formyl, acetyl, benzoyl, nitrobenzoyl and chlorinated benzoyl; and R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, pyridine, ammonium, lower aliphatic hydrocarbon amine, lower alkanol amine and aniline.

The most preferred compounds are those with the following structure:

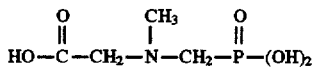

The lower alkylamine salts, in particular the isopropyl amine salts, are preferred.

These compounds are prepared according to the method described in U.S. Pat. No. 3,794,758 issued to Franz, Dec. 10, 1974.

C. DOSAGE

Any suitable dosage may be given in the method of the invention. The type of compound and the carrier and the amount will vary widely depending on the species of the warm blooded animal or human, body weight, and tumor being treated. Generally a dosage of between about 2 milligrams (mg) per kilogram (kg) of body weight and about 400 mg per kg of body weight is suitable. Preferably from 15 mg to about 150 mg/kg of body weight is used. Generally, the dosage in man is lower than for small warm blooded mammals such as mice. A dosage unit may comprise a single compound or mixtures thereof with other compounds or other cancer inhibiting compounds. The dosage unit can also comprise diluents, extenders, carriers and the like. The unit may be in solid or gel form such as pills, tablets, capsules and the like or in liquid form suitable for oral, rectal, topical or parenteral administration or intravenous administration or injection into or around the tumor site.

D. DOSAGE DELIVERY FORMS

The anti-cancer compounds are typically mixed with a pharmaceutically acceptable carrier. This carrier can be a solid or liquid and the type is generally chosen based on the type of administration being used. The active agent can be coadministered in the form of a tablet or capsule, as an agglomerated powder or in a liquid form. Examples of solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of liquid dosage forms include solutions or suspensions in water, pharmaceutically acceptable fats and oils, alcohols or other organic solvents, including esters, emulsions, syrups, elixirs, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners and melting agents. Oral dosage forms would contain flavorants and coloring agents. Parenteral and intravenous forms would also include minerals and other materials to make them compatible with the type of injection or delivery system chosen.

Specific examples of pharmaceutical acceptable carriers and excipients that may be used to formulate oral dosage forms of the present invention are described in US. Pat. No. 3,903,297 to Robert, issued Sep. 2, 1975. Techniques and compositions for making dosage forms useful in the present invention are described in the following references: 7 Modern Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

E. METHOD OF TREATMENT

The method of treatment can be any suitable method which is effective in the treatment of the particular virus or tumor type that is being treated. Treatment may be oral, rectal, topical, parenteral, intravenous or injection into or around the tumor site and the like. The method of applying an effective amount also varies depending on the tumor being treated. It is believed that parenteral treatment by intravenous, subcutaneous, or intramuscular application, formulated with an appropriate carrier, additional cancer inhibiting compound or compounds or diluent to facilitate application will be the preferred method of administering the compounds to warm blooded animals.

The following examples are illustrative and are not meant to be limiting to the invention.

Colon, Breast and Lung Tumor Cells Test

The following cell culture tests were performed to test the toxicity of the N-phosphonoglycine compounds on colon, breast and lung human tumor cells. The viability of the cells were tested by looking at MTT (3-[4,5-dimethylthiazol-2-yl]-2,5-diphenyltetrazolium bromide) reduction. MTT assay is a well known measure of cell viability.

The colon tumor cells (HT29 from American Type Culture Collection (ATCC)) and the breast cells (MX1 from cell lines from ATCC) were cultured in Eagle's Miminal Essential Medium with 10% fetal bovine serum. The lung tumor cells (A549 from ATCC cell lines) were cultured in Ham's F12 medium with 10% fetal bovine serum.

The tumor cells were passaged and seeded into culture flasks at the desired cell densities. The culture medium was decanted and the cell sheets were washed twice with phosphate buffered saline (PBS). The cells were trypsinized and triturated prior to seeding the flasks. Unless otherwise indicated the cultures were incubated at 37°±1° C. in a humidified atmosphere of 5±1% carbon dioxide in air. The cultures were incubated until they were 50–80% confluent.

The cells were subcultured when the flasks were subconfluent. The medium was aspirated from the flasks and the cell sheets rinsed twice with PBS. Next, the Trypsin Solution was added to each flask to cover the cell sheet. The Trypsin Solution was removed after 30–60 seconds and the flasks were incubated at room temperature for two to six minutes. When 90% of the cells became dislodged, growth medium was added. The cells were removed by trituration and transferred to a sterile centrifuge tube. The concentration of cells in the suspension was determined, and an appropriate dilution was made to obtain a density of 5000 cells/ml. The cells were subcultured into the designated wells of the 96-well bioassay plates (200 microliter cell suspension per well). PBS was added to all the remaining wells to maintain humidity. The plates were then incubated overnight before test article treatment.

Each dose of test article was tested by treating quadruplicate wells of cultures with 100 microliter of each dilution. Those wells designated as solvent controls received an additional 100 microliter of methanol control; negative controls wells received an additional 100 microliters of treatment medium. PBS was added to the remaining wells not treated with test article or medium. The plates were then incubated for approximately 5 days.

At the end of the 5 day incubation, each dose group was examined microscopically to assess toxicity. A 0.5 mg/ml dilution of MTT was made in treatment medium, and the dilution was filtered through a 0.45 micrometer filter to remove undissolved crystals. The medium was decanted from the wells of the bioassy plates. Immediately thereafter, 2000 microliter of the filtered MTT solution was added to all test wells except for the two untreated blank test wells. The two blank wells received 200 microliters of treatment medium. The plates were returned to the incubator for about 3 hours. After incubation, the MTT containing medium was decanted. Excess medium was added to each well and the plates were shaken at room temperature for about 2 hours.

The absorbance at 550 nm ($OD_{550}$) of each well was measured with a Molecular Devices (Menlo Park, Calif.) VMax plate reader.

The mean $OD_{550}$ of the solvent control wells and that of each test article dilution, and that of each of the blank wells and the positive control were calculated. The mean $OD_{550}$ of the blank wells was subtracted from the mean of the solvent control wells, and test article wells, respectively to give the corresponding mean $OD_{550}$.

% of Control=corrected mean $OD_{550}$ of Test Article Dilution$_{x100}$ corrected mean of $OD_{550}$ of Solvent Control Dose response curves were prepared as semi-log plots with % of control on the ordinate (linear) and the test article concentration on the abscissa (logarithmic). The $EC_{50}$ was interpolated from the plots for each test article.

For the test articles administered in methanol, separate responses were prepared to correct for the methanol data.

Adriamycin was used as a positive control. In all cases, it was more toxic than any of the test materials by one or two logs. Adriamycin is one of the more potent agents in current use and one with significant side effects. The peak plasma concentration of other, quite effective chemotherapeutic agents may be 10 to 50 times higher than that of Adriamycin.

The EC-50 is the concentration at which one half the cells are killed.

TABLE 1

| Test Material | EC-50 Result (ppml) | | | | | |
|---|---|---|---|---|---|---|
| | HT29 | HT29 | MX1 | MX1 | A549 | A549 |
| Adriamycin | 0.003 | 0.006 | 0.02 | 0.001 | 0.03 | 0.009 |
| glyophsate | 5.41 | 3.73 | 36.5 | 14.6 | 25.9 | 22.3 |

In normal healthy cells, the following results were obtained:

TABLE 2

| | EC-50 | | | | | |
|---|---|---|---|---|---|---|
| Test Material | Broncheal Cells | | Kerotinoyle Cells | | Fibroblasts | |
| glyphosate | 1.59 | 3.54 | 3.09 | 3.21 | 86.1 | 35.8 |
| Adriamycin | 0.015 | 0.0020 | 0.0035 | 0.0093 | 0.065 | 0.10 |

These experiments show that these compositions are effective in killing tumor cells without significantly affecting healthy cells. They are safer than adriamycin.

It is believed that many herbicides alone or in combination with other herbicides and fungicides will slow this beneficial anti-tumor effect.

The N-phosphonoglycine derivatives are also effective against viruses including rhinovirus, HIV, herpes, and influenza. The dosage form and method of treatment is the same as for tumors or cancer.

What is claimed is:

1. A method of treating cancer in warm blooded mammals comprising administering a safe and effective amount of a pharmaceutical composition comprising a N-phosphonoglycine derivatives of the formula:

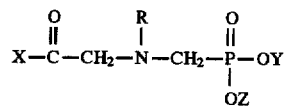

wherein X is selected from the group consisting of hydroxyl, alkoxy or chloroxy up to 12 carbon atoms; lower alkenoxy, cyclohexyloxy, morpholino, pyrrlidinyl, piperidino and NHR'; Y and Z each independently selected from hydrogen and lower alkyl; and R is selected from the group consisting of hydrogen, formyl, acetyl, benzoyl, nitrobenzoyl and chlorinated benzoyl; and R' is selected from the group consisting of hydrogen, lower alkyl and lower alkenyl, cyclohexyl, phenalkyl of up to 8 carbon atoms, phenyl, chlorinated phenyl and anisyl; and certain salts of these compounds, which salts are selected from the group consisting of the Group I and II metals having an atomic number of up to 30, hydrochloride, salicylate, acetate, pyridine, ammonium, lower aliphatic hydrocarbon amine, lower alkanol amine and aniline.

2. A method according to claim 1 wherein said N-phosphonoglycine is administered orally or enterically.

3. A method according to claim 2 wherein said N-phosphonoglycine is administered in a solid form.

4. A method according to claim 3 wherein said solid form includes a carrier selected from the group consisting of lactose, sucrose, gelatin and agar.

5. A method according to claim 3 wherein from about 15 mg/kg to about 150 mg/kg of said N-(phosphonomethyl) glycine is administered.

6. A method according to claim 2 wherein N-phosphonoglycine is administered in a liquid form.

7. A method according to claim 6 wherein said liquid dosage form is selected from the group consisting of aqueous solutions, emulsions, suspension solutions, and suspensions reconstituted from non-effervescent and effervescent preparations and suspensions in pharmaceutically acceptable fats or oils.

8. A method according to claim 7 wherein said liquid dosage from a member selected from the group consisting of suspending agents, diluents, sweeteners, flavorants, colorants, preservatives, emulsifying agents and coloring agents, and mixtures thereof.

9. A method according to claim 1 wherein said N-phosphonoglycine is N-(phosphonomethyl) glycine isopropyl amine salt.

10. A method of treating cancer in warm blooded mammals comprising administering a safe and effective amount of N-(phosphonomethyl)glycine.

11. A method of treating cancer in warm blooded mammals according to claim 10 wherein from about 2 mg/kg body weight to about 400 mg/kg of said N-(phosphonomethyl)glycine is administered.

12. A method according to claim 11 wherein said N-(phosphonomethyl)glycine is administered orally or enterically.

13. A method according to claim 12 wherein said N-(phosphonomethyl)glycine is administered in a solid form.

14. A method according to claim 13 wherein said solid form includes a carrier selected from the group consisting of lactose, sucrose, gelatin and agar.

15. A method according to claim 14 wherein from about 15 mg/kg to about 150 mg/kg of said N-(phosphonomethyl) glycine is administered.

16. A method according to claim 12 wherein said N-(phosphonomethyl)glycine is administered in a liquid form.

17. A method according to claim 16 wherein said liquid dosage form is selected from the group consisting of aqueous solutions, emulsions, suspension solutions, and suspensions reconstituted from non-effervescent and effervescent preparations and suspensions in pharmaceutically acceptable fats or oils.

18. A method according to claim 17 wherein said liquid dosage from a member selected from the group consisting of suspending agents, diluents, sweeteners, flavorants, colorants, preservatives, emulsifying agents and coloring agents, and mixtures thereof.

* * * * *

UNITED STATES PATENT AND TRADEMARK OFFICE
CERTIFICATE OF CORRECTION

PATENT NO. : 5,665,713
DATED : September 9, 1997
INVENTOR(S) : James Berger Camden It is certified that error appears in the above-identified patent and that said Letters Patent is hereby corrected as shown below:

Column 6,
Line 37, delete "derivatives" and insert in lieu thereof -- derivative --.
Line 45, delete "chloroxy" and insert -- in lieu thereof -- chloroalkoxy --.
Line 45, immediately after "atoms", delete the semicolon ";", and insert in lieu thereof, a comma -- , --.
Line 46, delete "pyrrlidinyl" and insert in lieu thereof -- pyrrolidinyl --.
Line 47, insert -- are -- immediately after "independently".
Line 51, delete "and" and insert in lieu thereof -- , --.

Column 7,
Line 1, immediately after "wherein", insert -- said --.
Line 5, delete "and".
Line 6, delete "and" and insert in lieu thereof -- or --.
Line 7, insert a comma -- , -- immediately after "preparations".
Line 10, delete "from a member" and insert in lieu thereof, -- form is --.
Line 12, delete "and" and insert in lieu thereof a comma -- , --.

Column 8,
Line 16, delete "and".
Line 17, delete "and" and insert in lieu thereof -- or --.
Line 18, insert a comma -- , -- immediately after "preparations".
Line 21, delete "from a member" and insert in lieu thereof, -- form is --.
Line 23, delete "and" and insert in lieu thereof a comma -- , --.

Signed and Sealed this

Sixteenth Day of July, 2002

*Attest:*

*Attesting Officer*

JAMES E. ROGAN
*Director of the United States Patent and Trademark Office*